(12) United States Patent
Maruyama et al.

(10) Patent No.: US 6,776,790 B1
(45) Date of Patent: Aug. 17, 2004

(54) UV RADIATION TREATMENT APPARATUS

(75) Inventors: Shinichi Maruyama, Saitama (JP); Yoshihiro Sakurai, Shinjuku-ku (JP)

(73) Assignee: Kabushiki Kaisha Lucent, Saitama (JP)

( * ) Notice: Subject to any disclaimer, the term of this patent is extended or adjusted under 35 U.S.C. 154(b) by 0 days.

(21) Appl. No.: 10/452,537

(22) Filed: Jun. 2, 2003

(51) Int. Cl.[7] .................................................. A61N 5/06
(52) U.S. Cl. .............................. 607/94; 606/9; 607/91
(58) Field of Search ........................... 606/9; 607/88–94

(56) References Cited

U.S. PATENT DOCUMENTS

| | | | | |
|---|---|---|---|---|
| 3,101,716 A | * | 8/1963 | Cornell, Jr. ................... | 607/91 |
| 5,466,248 A | * | 11/1995 | Whitson-Newman ........ | 607/88 |
| 6,273,906 B1 | * | 8/2001 | Swanson ..................... | 607/91 |
| 6,676,687 B2 | * | 1/2004 | Stoppler ..................... | 607/94 |
| 2003/0088297 A1 | * | 5/2003 | Stoppler ..................... | 607/94 |

* cited by examiner

*Primary Examiner*—Lee Cohen
*Assistant Examiner*—Henry M Johnson, III
(74) *Attorney, Agent, or Firm*—Jordan and Hamburg LLP

(57) ABSTRACT

A UV treatment comprises an upper case 2 of a size allowing right and left feet to be placed thereupon, a bottom case 2 that supports the upper case 2, and a cover 3 attached to the upper case 2. Two front position UV radiation ports 10L and 10R that open in the up-down direction are provided on both the right and left sides at the front of the upper case 2. Central UV radiation ports 15L and 15R that open in the left and right direction are provided in the left-right direction center toward the back of the upper case 2. UV lamps 20L and 20R are disposed on the bottom case 3 in positions corresponding to the front position UV radiation ports 10L and 10R, and a UV lamp 20 is disposed at a position corresponding to the central UV radiation ports 15L and 15R. When left and right feet are placed above the front radiation ports 10L and 10R of the upper case 2, both the front of a foot and the inner sole can be irradiated simultaneously.

3 Claims, 3 Drawing Sheets

UV RADIATION TREATMENT APPARATUS

BACKGROUND OF INVENTION

1. Field of Invention

The present invention relates to a UV-radiation treatment apparatus for household use used to treat athlete's foot.

2. Background Art

Athlete's foot, which frequently occurs in such places as toes and the inner sole, is an affliction caused by the parasitic presence on the skin of a fungus of the genus trichophyton. It is known that trichophyton fungus can be killed through UV irradiation, and a variety of UV ray treatment apparatuses have heretofore been developed.

FIG. 4 shows a simplified vie of one example of such a conventional UV ray treatment apparatus that can be used at home, configured so that a treatment apparatus body (a) is formed in a columnar shape having a size allowing for manual holding and use; a UV lamp (d) is attached to a tip thereof, and an ON switch (b) and an OFF switch (c) are provided on an outer surface of such treatment apparatus body (a); through operation of such switches the UV lamp is turned on and off. In addition, a cylindrical lamp cover (f) that covers the UV lamp (d) is attached to a tip of the treatment apparatus main body (a). A UV radiation port (e) is provided on an end surface of such lamp cover (d), enabling UV radiation outward. When the UV radiation port is directed at the toes or other afflicted area and the UV lamp (d) is turned on, the afflicted area is irradiated with UV rays.

However, when the above conventional household UV treatment apparatus is used, a user is forced to maintain an uncomfortable posture, with the device held in the hand, for the entire time that the afflicted area is being irradiated with UV rays; when the treatment is lengthy, the task will be quite laborious. What is more, the afflicted parts of both feet cannot be treated at the same time by a single UV treatment apparatus; in fact, differing afflicted parts of the same foot, such as the toes and inner sole, cannot be treated simultaneously. Thus there is the problem that therapy requiring much time is needed to treat all afflicted areas.

It is an object of the present invention to provide a UV treatment apparatus that enables simultaneous UV irradiation of both feet and enables simultaneous UV irradiation of differing afflicted parts of the same foot, as in the toes and inner sole.

SUMMARY OF THE INVENTION

In order to solve the above-described problems, the present invention is constituted so that a treatment apparatus body is formed from an upper case on which both right and left feet are placed, a bottom case supporting such upper case, and a cover that covers the front upper surface of the upper case; front position UV radiation ports are provided toward the front of the treatment apparatus upper case so as to enable UV radiation in the up-down direction, and central UV radiation ports are provided at a central position toward the rear of the upper case so as to enable UV radiation in the right-left direction. In addition, UV lamps are disposed between the upper case and bottom case at positions corresponding to the front position UV radiation ports and central UV radiation ports; when the UV lamps are turned on, UV radiation is directed through the UV radiation ports and upwards from the upper case. The upper case, having a size allowing for areas for both feet to be placed thereupon, is supported by the bottom case, and the front part of the upper surface thereof is covered by a cover; the front-position UV radiation ports open in the up-down direction in a front portion of the areas of the upper case on which both feet are placed.

When a foot is inserted toe-first into the space between the cover and upper case and placed on the upper case, and the UV lamps are turned on, the front part of the foot is irradiated by UV rays coming from the front position UV radiation ports, and, simultaneously, the inner sole is irradiated by UV rays coming from the central UV radiation ports. Thus the front of the foot and the sole can be treated.

Further, sensors that turn on the UV lamps for a set period of time are provided, respectively, in the areas for placing the right foot and the left foot; insertion of foot between upper case and cover is detected by the respective sensor, which causes only the UV lamp positioned at the relevant front position UV radiation port to turn on; with such a constitution, only the lamp for an area into which a foot has been inserted and placed is turned on.

Further, a fan that is driven when a sensor turns on a UV lamp is provided between the upper case and bottom case, and external air that the fan draws into the space between the upper case and bottom case is emitted from the UV radiation ports; with such a configuration, wind caused by the fan is blown out from the UV radiation ports, provides a drying effect to the afflicted areas.

DETAILED EXPLANATION OF THE INVENTION

The present invention will be explained with reference made to the drawings.

Figure 1:
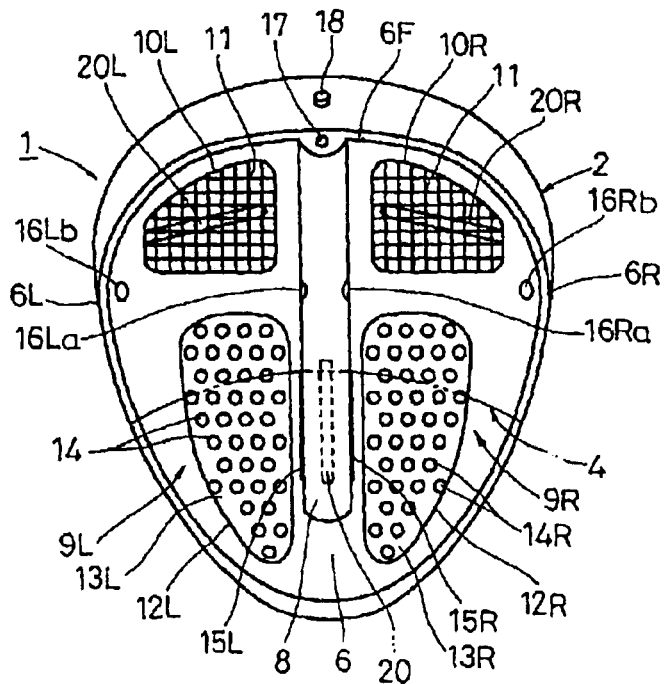
FIG. 1 is a plan diagram showing one embodiment of a UV radiation treatment apparatus according to the present invention, in a state with the cover removed.
Figure 2:
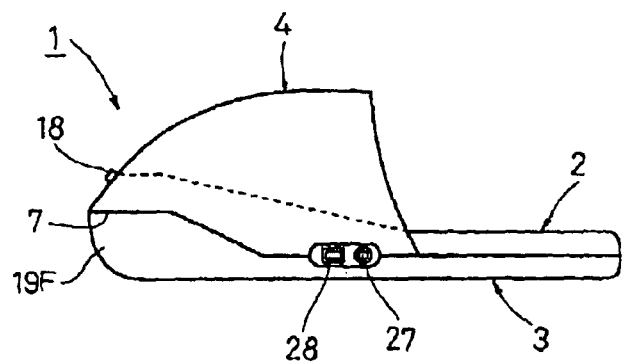
FIG. 2 is a lateral view showing the full UV radiation treatment apparatus of FIG. 1.
Figure 3:
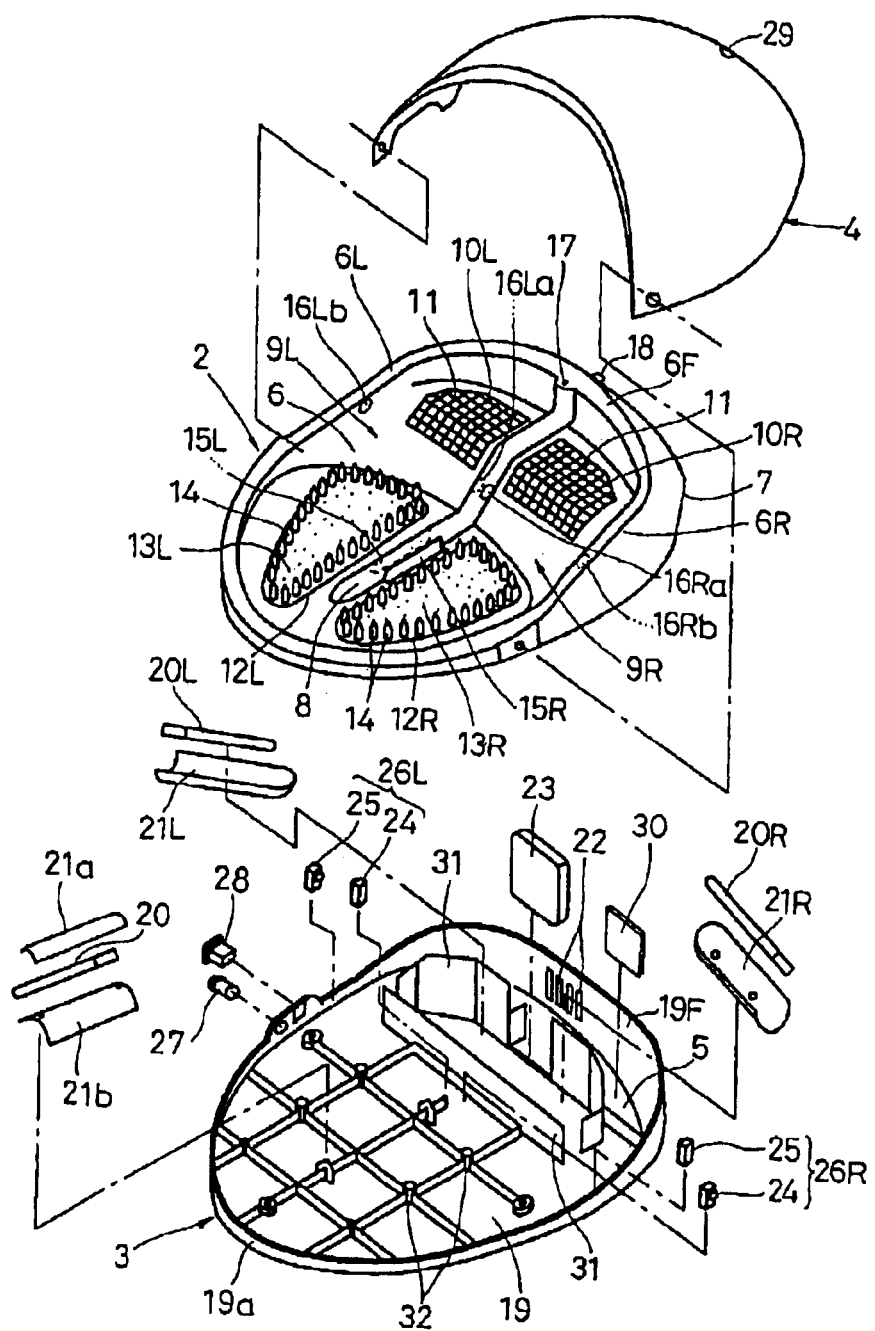
FIG. 3 is an exploded oblique view showing the full UV radiation treatment apparatus of FIG. 1.
Figure 4:
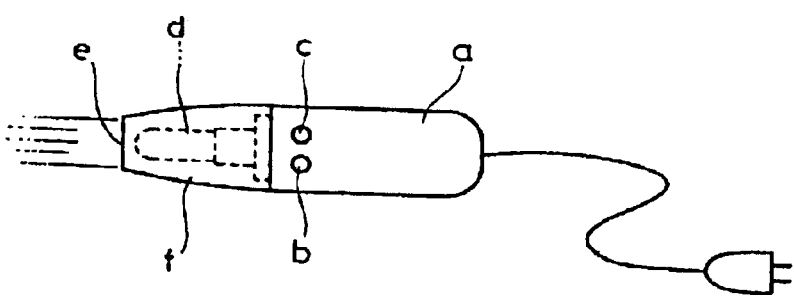
FIG. 4 is a schematic view showing one example of a conventional UV radiation treatment apparatus.

FIGS. 1 to 3 show one embodiment of a UV radiation treatment apparatus according to the present invention. A UV radiation treatment apparatus 1 comprises an upper case 2, a bottom case 3 and a cover 4. The upper case 2 has a flat, egg shape, with a size enabling areas for placing a left and right foot to be formed thereupon. The bottom case 3 is constituted so as to be able to support the upper case 2 and so that a requisite space 5 is formed toward the front between the bottom case 3 and the upper case 2. The cover 4 has a curved shape that enables it to cover the entire top of a foot placed on the upper case 2 from the toes to the base of the ankle, and is removably attached to the front upper surface of the upper case 2.

The upper case 2 is configured as follows. A base plate 6 has a step-like configuration so that the front side is higher than the back side; the peripheral edge thereof has a double-shell construction, first bending upwards, then bending outwards, and then bending downwards; those portions of this double-shelled peripheral edge that extend from a front edge 6F to an intermediate position on the left and right side edges 6L and 6R have a slightly higher height; further, formed on the front edge 6F is an engagement part 7 the downward-bending part of which has a shorter length and which engages with a front wall 19F of the bottom case 3 (discussed below). In the right-left direction center of the base plate 6, a rib 8 is formed having a semicircular cross-section, projecting upwards and extending from the front edge 6F to near the rear end; this rib 8 serves as a border between a left-foot area 9L for placing the left foot and a right-foot area 9R for placing the right foot. Front position UV radiation ports 10L and 10R are provided on the base plate 6 towards the front of the left/right foot areas 9L and 9R, said UV radiation ports 10L and 10R having a size that corresponds to the toe area; towards the rear of the left/right foot areas 9L and 9R are provided recesses (or hollows) 12L and 12R having a size that corresponds to the range from arch to heel. A mesh plate 11 is attached to the openings of the UV radiation ports 10L and 10R so that the openings of the UV radiation ports 10L and 10R have a mesh structure; also, foot plates (stepping plates) 13L, 13R having multiple small projections 14 on the upper surfaces thereof, are removably disposed on the recesses 12L and 12R. Thus left and right feet can be placed on top of the front position UV radiation ports 10L and 10R and foot plates 13L and 13R. Further, on the left and right sides of the rib 8 disposed between the left/right foot plates 13L and 13R, central UV radiation ports 15L and 15R are respectively formed, which extend in a slit shape in the front-back direction. In an intermediate position in the front-back direction of the rib 8, a sensor hole 16La that opens towards the left foot area 9L and a sensor hole 16Ra that opens towards the right foot area 9R are provided, and sensor holes 6Lb and 16Rb are provided on the inner shell portion of left and right side edges 6L and 6R so as to face each other in the right-left direction. Further, on the front edge 6F of the upper case 2, which forms the front end of the rib 8, a power supply pilot light 17 and a restart switch 18 are provided.

The bottom case 3 is configured as follows. On the peripheral edge of a base 19 a flange wall 19a is provided that receives the peripheral edge of the base plate 6 of the upper case 2; a front wall part 19F of the flange wall 19a is formed at a height enabling insertion into and engagement with the engagement part 7 on the front edge 6F of the upper case 2; by placing the upper case 2 on the flange wall 19a so that it is supported thereby, a requisite space 5 is formed between the front portion of the upper case base plate 6 and the bottom case base 19. UV lamps 20L and 20R are disposed at a front position of the base 19, at positions aligned with the left/right front position UV radiation ports 10L and 10R of the upper case 2, with reflectors 21L and 21R interposed the base and the lamps; UV radiation from the UV lamps 20L and 20R passes through the front position UV radiation ports 10L and 10R and radiates upwards from the upper case 2. In the right-left direction center towards the rear of the base 19, one UV lamp 20 sandwiched and supported by upper and lower reflectors 21a and 21b is disposed below (inside) the rib 8 in alignment with the central UV radiation ports 15L and 15R which open toward the left and right of the rib 8 of the upper case 2; UV radiation from the UV lamp 20 radiates to the left and right through the central radiation ports 15L and 15R on the rib 8. On a central part of the front wall 19F of the base 19, multiple through holes 22 are provided; a fan 23 is provided on the base 19 on the inside of the through holes 22; when the fan 23 is driven, air drawn into the space 5 through the through holes 22 is blown out through the left-right front position UV radiation ports 10L and 10R into the upper case 2 and, passing below the rib 8, is blown out through the central UV radiation ports 15L and 15R toward the upper case 2. Further, at front-back direction intermediate positions of the base 19, photoelectric sensors 26L and 26R are disposed in alignment with sensor holes 16La, 16Lb and 16Ra, 16Rb of the upper case 2, such sensors each comprising a light-emitter 24 and a light-receiver 25. On either the right side or left side of flange wall 19a of the base 19, a DC input jack 27 into which the DC plug of an AC adapter (not shown in figures) is inserted and a power switch 28 that turns on the power pilot light 17 when turned on are provided.

The cover 4 is made from a semi-translucent resin that cuts UV rays; it includes a small hole 29 that allows the restart switch 18 to be exposed.

A UV treatment apparatus according to the present invention includes a control plate 30 accommodated within the space 5. Commands from the control plate 30 cause the UV lamps 20L, 20R and 20 and the fan 23 to turn on and off. When the power switch 28 is turned on, the control plate 30 causes the power pilot light 17 to turn on; in such a state, when the sensor 26L is ON, the fan 23 is driven and the UV lamps 20L and 20 are turned on; when the sensor 26R is on, the fan 20 is activated and the UV lamps 20R and 20 are turned on; when an amount of time (e.g., 1 min) as set by a timer (not shown in the drawings) elapses, a buzzer (not shown in the drawings) sounds, the drive of the fan 23 is stopped and UV lamps 20L, 20R and 20, which were on, are turned off. When the time set by the timer elapses, the apparatus can be restarted by turning the restart switch 18 on, with feet still within the cover 4, or by removing and then reinserting feet.

For the UV lamps 20L, 20R and 20, quartz high voltage discharge tubes are used. In FIG. 3, the indicator 31 indicates a spacer/UV lamp heat-blocking wall provided in the front part of the space 5 so as to support the upper case 2, for the purpose of maintaining the space 5 between the upper case 2 and the bottom case 3; 32 indicates spacers provided on the base 19 for maintaining a space with the requisite thickness toward the rear between the upper case 2 and bottom case 3.

When a UV treatment apparatus according to the present invention thus configured is used to treat athlete's foot, the UV treatment apparatus according to the present invention is placed, for example, on the floor, the power switch 28 is turned on and confirmation is made that the pilot lamp 17 is on; then the feet of a patient seated, for example, in a chair, are inserted into the cover 4. If only one foot is to be treated, the appropriate foot is inserted into either the left foot area 9L or the right foot area 9R on the upper case 2; when both feet are to be treated, both feet are inserted into the left and right foot areas 9L and 9R.

In such a case, insertion of left foot into the left foot area 9L is detected by the sensor 26L, thus causing the fan 23 to be driven and the UV lamps 20L and 20 to be turned on; insertion of right foot into the right foot area 9R is detected by the sensor 26R, thus causing the fan 23 to be driven and the UV lamps 20R and 20 to be turned on. When both feet are inserted into the left and right foot areas 9L and 9R, the fan 23 is driven and all UV lamps 20L, 2OR and 20 are turned on. Therefore, selection can be made to treat just one foot or to treat two feet.

Let us suppose that both left and right feet have been inserted into the left and right foot areas 9L and 9R. The front part of the feet are placed on the left and right front side UV lamp radiation ports 10L and 10R, which have a mesh construction, and the parts of the feet from the arch to the heel are placed on the foot plates 13L and 13R. Thus the bottoms of the left and right feet front portions are irradiated by UV radiation from the left and right UV lamps 20L and 20R passing through the left and right front position UV radiation ports 10L and 10R; and the inner arch of both feet are irradiated by UV radiation from the UV lamp 20 disposed on the bottom of the rib 8, such radiation passing through the central UV radiation ports 15L and 15R that open in the right-left direction. At this time, external air is drawn into the space 5 by operation of the fan 23 through the through holes 22 provided in the front wall 19F of the bottom case 3; the drawn-in air is blown upwards through the left and right front position UV radiation ports 10L and 10R, and passing through the space beneath the rib 8 is blown in the left-right direction from the central UV radiation ports 10L and 10R; therefore, both the front portion of the feet and the inside portion of the soles are dried by the wind that strikes them.

When treatment by the UV lamps 20L, 20R and 20 has been performed for a set time with the fan 23 in a driven state, a buzzer sounds, and the drive of the fan 23 is stopped, and the UV lamps 20L, 20R and 20 are turned off. When treatment is to be continued further, the restart switch is turned on, with feet still inserted, or the feet may be removed and then re-inserted.

As described above, treatment can be performed with a patient seated in a chair or the like, making the treatment much more comfortable, without the patient being forced into an uncomfortable posture, as was the case with treatment using a conventional apparatus. In addition, when treating both feet, or when treating different parts of the same foot, as in the front section and the inner sole, the treatment can be done at once, in a shorter time. Moreover, the foot plates 13L and 13R are removable, allowing for periodic cleaning to maintain hygiene.

The present invention should not be construed as limited to the above-described embodiment. For example, the embodiment shows a case where a fan 23 is provided, and the fan 23 is driven simultaneously with the turning on of the UV lamps 20L, 20R and 20 by the sensors 26L and 26R. However, the apparatus may be configured without the fan 23, and treatment performed by the sensors 26L and 26R causing the UV lamps 20L, 20R and 20 to go on, and of course the sensors 26L and 26R can be of a type other than photoelectric, such as pressure sensitive or other type of sensor; the UV radiation ports 10L and 10R having a mesh construction may be constituted by a plurality of densely packed holes made directly in the base plate 6; and a variety of other modifications may be enacted provided that they do not deviate from the gist and spirit of the present invention.

As described above, a UV treatment apparatus according to the present invention offers the following outstanding effects.

(1) A treatment apparatus body is formed from an upper case on which both left and right feet can be placed, a bottom case supporting the upper case, and a cover that covers the front side upper surface of the upper case. Front side radiation ports are provided on a front side position of the upper case of the treatment apparatus body, so as to radiate UV light in the up-down direction, and central UV radiation ports are provided in a central part of the rear section of the upper case, so as to radiate UV rays in the right-left direction. Further, between the upper case and bottom case, UV lamps are disposed at positions aligned with the front side and central UV radiation ports. With such a constitution, when the lamps are turned on, UV radiation is directed upwards from the upper case, through the UV radiation ports; further, because the upper case is of sufficient dimensions to enable it to have areas for placing both the right and left feet; because it is supported by the bottom case and the front side portion thereof is covered by the cover; and because front position UV radiation ports opening in the up-down direction are provided toward the front of the area where the right and left feet are placed, insertion of a foot between the cover and upper case and placing of foot on the upper case enables the front of the foot to be treated at the same time as the inner sole, the former being irradiated through the front position UV radiation ports and the latter being irradiated through the central UV radiation ports. Such a constitution provides the benefit of enabling differing parts of the foot to be effectively treated within a short time, and allows a patient to remain seated in, for example, a chair during treatment, not forcing that person to assume an uncomfortable posture during treatment.

(2) Sensors that turn on the UV lamps for a set period of time are provided, respectively, in the areas of the upper case where the right and left feet are to be placed. When a foot is inserted between the upper case and cover, a sensor detects such insertion, and causes the UV lamp positioned at the relevant front position UV radiation port to turn on. With such a constitution, only the UV lamp corresponding to a foot area into which a foot has been inserted will be turned on; therefore, the apparatus provides the convenience of allowing a choice of which feel will get treated, whether a single foot or both feet simultaneously.

(3) Between the upper case and bottom case, a fan is provided that is driven simultaneously with the turning on of the UV lamps by a sensor; external air drawn in by the fan into the space between the upper case and lower case is emitted through the UV radiation ports. With such a constitution, wind generated by the fan is emitted through the UV radiation ports, and such wind strikes the afflicted areas, providing a drying effect.

What is claimed is:

1. A UV treatment apparatus comprising a treatment apparatus body formed from an upper case onto which right and left feet are placed, a bottom case that supports said upper case, and a cover that covers the front upper surface of said upper case, wherein front position UV radiation ports are provided in a front position of said UV treatment apparatus upper case so as to enable radiation in the up-down direction and central UV radiation ports are provided in a rear position of such upper case so as to enable radiation in the right-left direction and, further, between said upper case and bottom case, UV lamps are disposed in respective alignment with said front position UV radiation ports and central UV radiation ports, and when said UV lamps are turned on, UV radiation is directed through said UV radiation ports upwards from the upper case.

2. A UV treatment apparatus according to claim 1, comprising sensors for causing UV lamps to be on for a set period of time respectively provided at the right and left foot placing areas on the upper case, wherein said sensors detect insertion of a foot between said upper case and cover and cause a UV lamp positioned at a front position UV radiation port to turn on.

3. A UV treatment apparatus according to claim 2, comprising a fan that is driven simultaneously with the turning on the UV lamps by the sensors, wherein external air drawn into a space between the upper case and bottom case by the fan's being driven is emitted through the UV radiation ports.

* * * * *